United States Patent [19]

Mesek

[11] Patent Number: 4,938,754
[45] Date of Patent: Jul. 3, 1990

[54] DISPOSABLE DIAPER WITH IMPROVED BODY COMFORMITY AND LIQUID RETENTION

[75] Inventor: Virginia R. Mesek, Oak Forest, Ill.

[73] Assignee: McNeil-PPC, Inc., Milltown, N.J.

[21] Appl. No.: 351,266

[22] Filed: May 10, 1989

Related U.S. Application Data

[63] Continuation of Ser. No. 196,898, May 18, 1989, which is a continuation of Ser. No. 942,964, Dec. 16, 1986, which is a continuation of Ser. No. 798,035, Nov. 14, 1985, which is a continuation of Ser. No. 565,448, Dec. 27, 1983, which is a continuation-in-part of Ser. No. 1,615, Jan. 8, 1974.

[51] Int. Cl.$^5$ .............................. A61F 13/16
[52] U.S. Cl. ................................. 604/385.2
[58] Field of Search ............ 604/385.1, 385.2, 366, 604/370, 358

[56] References Cited

U.S. PATENT DOCUMENTS

| | | | |
|---|---|---|---|
| Re. 31,922 | 6/1985 | Mesek et al. | 604/385.2 |
| 2,675,805 | 4/1954 | Trimble | 128/284 |
| 3,245,407 | 4/1966 | Mason | 128/284 |
| 3,417,751 | 12/1968 | Murdoch | 128/284 |
| 3,488,778 | 1/1970 | Goujon et al. | 128/284 |
| 3,695,269 | 10/1972 | Malaney | 128/284 |
| 3,860,003 | 1/1975 | Buell | 604/385.2 |
| 4,050,462 | 9/1977 | Woon et al. | 604/385.2 |
| 4,069,822 | 1/1978 | Buell | 604/385.2 |
| 4,205,679 | 6/1980 | Repke et al. | 604/385.2 |
| 4,210,143 | 7/1980 | DeJon kheere | 604/385.2 |
| 4,253,461 | 3/1981 | Strickland | 604/385.2 |
| 4,352,355 | 10/1982 | Mesek et al. | 604/385.2 |
| 4,397,645 | 8/1983 | Buell | 604/385.2 |
| 4,430,086 | 2/1984 | Repke | 604/385.2 |
| 4,490,148 | 12/1984 | Beckeström | 604/385.2 |

Primary Examiner—John D. Yasko

[57] ABSTRACT

A disposable diaper having improved fit and liquid containment provided by gathering means adjacent at least one edge of the absorbent panel, said gathering means including at least two separately extending, effectively elastic elements. Each of the effectively elastic elements applies a gathering force to a zone of the diaper, thereby defining multiple lines of gasketing about the leg or waist openings.

34 Claims, 6 Drawing Sheets

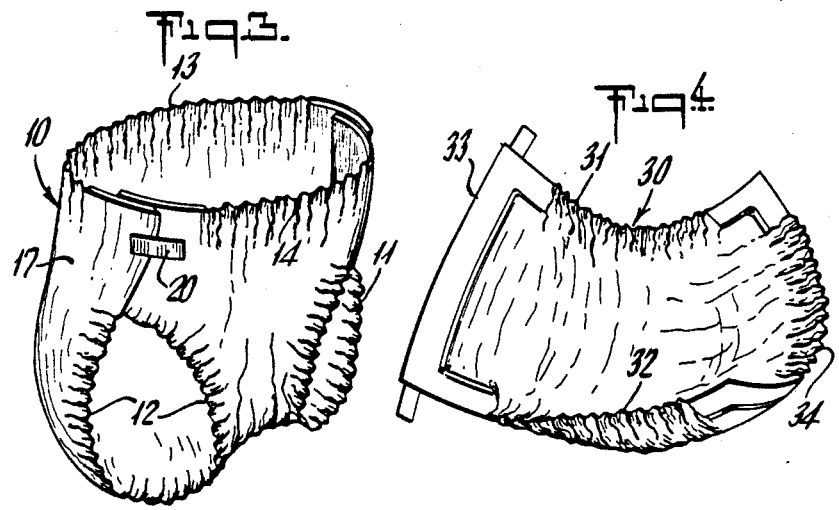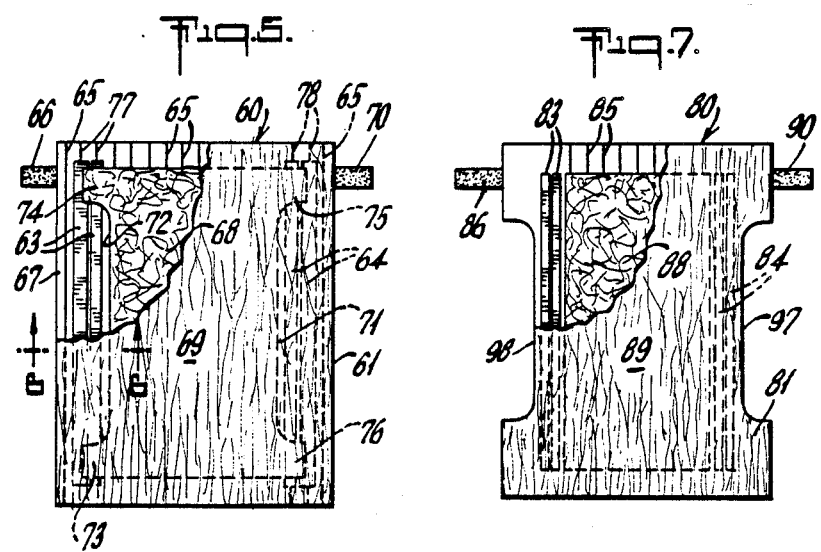

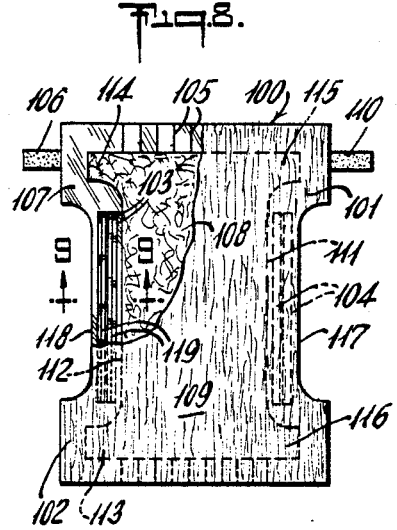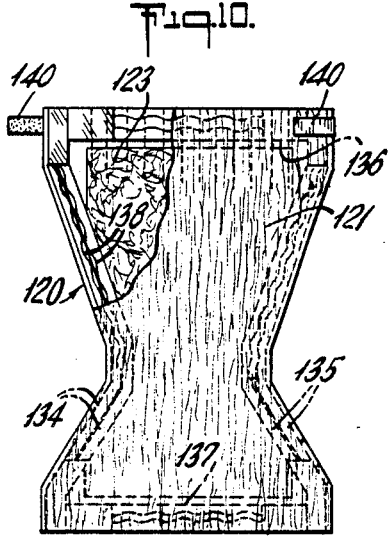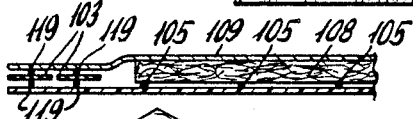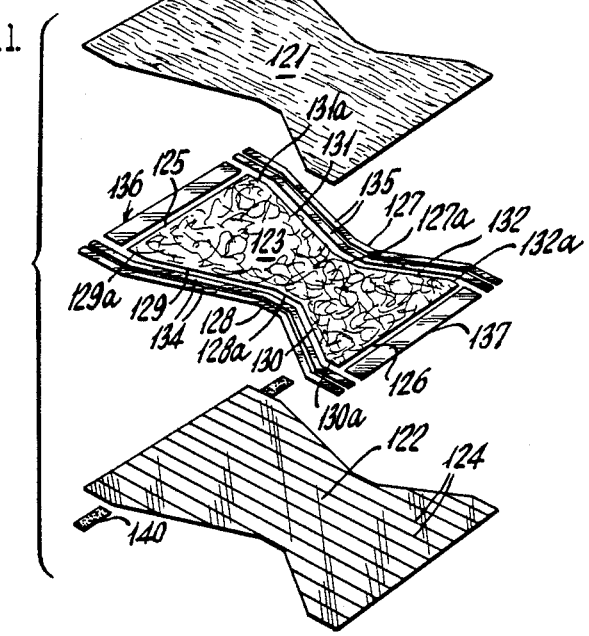

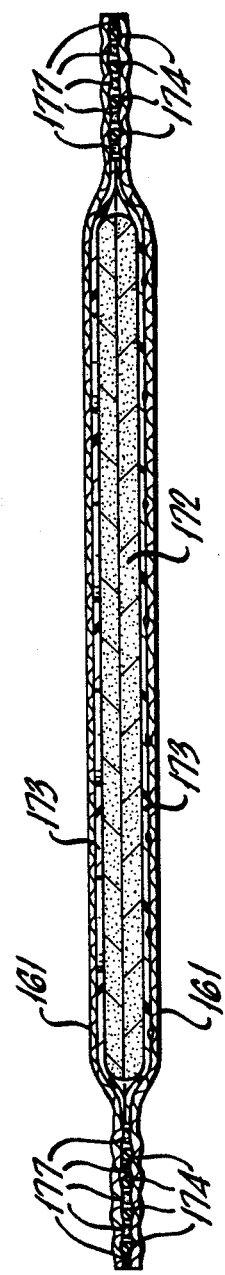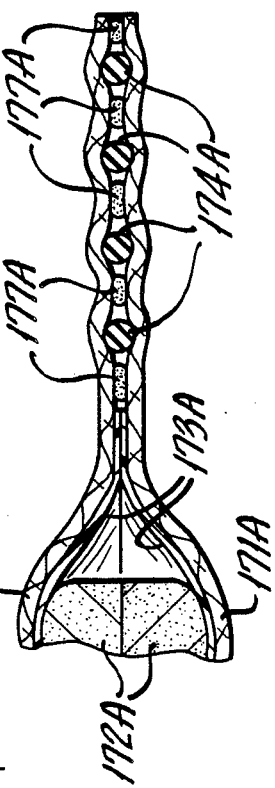
Fig. 15.
Fig. 15A.

DISPOSABLE DIAPER WITH IMPROVED BODY COMFORMITY AND LIQUID RETENTION

BACKGROUND OF THE INVENTION

This application is a continuation of application Ser. No. 196,898 filed May 18, 1989, which is a continuation of application Ser. No. 942,964 filed Dec. 16, 1986, which is a continuation of application Ser. No. 798,035 filed Nov. 14, 1985, which is a continuation of application Ser. No. 565,448 filed Dec. 27, 1983, which is a continuation-in-part of application Ser. No. 1615, filed Jan. 8, 1979. The present invention relates to improvements in disposable diapers which enable the diaper to closely conform to the torso of a baby. The diapers of the present invention accomplish this without causing any discomfort to the baby, while at the same time providing improved gasketing around the thighs resulting in improved liquid containment.

In the recent past disposable diapers have been introduced into the marketplace which have a narrow but relatively thick strip of elastic at each side thereof, so as to gather the side margins of the diaper in a manner similar to that of conventional moisture-impermeable panties. Such diapers are made generally in accordance with the teachings of U.S. Pat. No. 3,860,003. In order for the elastic members to be effective in such diapers, it is necessary that the elastic members be spaced relatively far from the side marginal edges of the absorbent panel of the diaper, and for the elastic members to be associated with thin, highly flexible facing and backing layers. As a result, when such diapers are placed upon a baby, the narrow but relatively thick elastic members cause a narrow band of the facing layer to bear against the baby's skin with substantially line contact. This results in a high degree of stress concentration that may cause pinching and irritation of the baby's skin.

The problems attributable to the unduly high compressive force caused by such narrow but relatively thick elastic strips of the prior art diapers mentioned above are particularly acute when the baby has voided and the diaper is wet. Because the backing and facing layers are so highly flexible, when the diaper is wet and conditions are present tending to cause hydration of the baby's skin, the narrow elastic members sometimes cause the facing layer to press against the skin with sufficient force to injure the skin. Also, the elastic members in prior art diapers of the type described above cause the diaper to gradually creep upwardly upon the baby's thighs. As a result, the forces applied to the skin by the stressed elastic members increase the longer the diaper is worn.

SUMMARY OF THE INVENTION

In addition to those elements which are present in currently commercially available products, i.e., a moisture-pervious facing adapted to engage the baby's skin, an absorbent batt or panel adjacent to the facing, and an outer moisture-impervious backing over the absorbent batt, the diapers of the present invention include gathering means about the leg and/or waist openings of the diaper which include at least two separate and distinct effectively elastic elements. Each of said elastic elements applies a gathering force to a zone of the diaper, thereby defining more than one line of gasketing.

The elastic members may be positioned in spaced parallel relationship with respect to one another and may substantially be parallel the straight or contoured edge of the diaper absorbent panel or facing layer. The elestic members may also be positioned in non-parallel relationship; for instance, when the edge of the absorbent panel is nonparallel with the edge of the diaper, at least one of the elastic members may be positioned parallel to the edge of the absorbent panel, and at least one elastic member may be positioned parallel to the edge of the diaper. It is also contemplated that the separately positioned elastic members which comprise the gathering means may be subjected to different degrees of stretch or elongation when secured to the diaper, providing even greater body conformity and wearer comfort.

Diapers constructed in accordance with the present invention have several unexpected advantages, particularly as compared to the prior art diapers of the type disclosed in U.S. Pat. No. 3,860,003. In this regard, by utilizing spaced multiple elastic members as the gathering means, the area of the facing that is pressed against the baby's skin is relatively large, distributing the force applied to the skin over a relatively large area and thereby minimizing the possibliity of irritation. Because of the relatively large area of facing engaging the baby's skin and the multiple gathering zones or lines of gasketing, improved liquid containment around the thighs and waist may be effected. In this regard, it is significant that absorptive materials effect at least in part the liquid containment, in contradistinction to the relatively non-absorbent facing in U.S. Pat. No. 3,860,003 which provides little, if any gasketing action. As will appear in more detail from the following description, diapers of the present invention provide improved fit, and an improved liquid seal around the baby's legs and/or waist without irritation to the baby's skin.

BRIEF DESCRIPTION OF THE DRAWINGS

In the drawings,

FIG. 3 is a perspective view of the diaper of FIG. 1 illustrating diaper configuration when applied about a baby;

FIG. 4 is a perspective view showing another embodiment of the disposable diaper of this invention;

FIG. 5 is a plan view of yet another embodiment of a disposable diaper of this invention with a portion broken away to show interior detail;

FIG. 6 is an enlarged partial cross-section of FIG. 5 taken along lines 6—6;

FIG. 7 is a plan view of a still further embodiment of a disposable diaper of this invention with a portion broken away to show interior detail;

FIG. 8 is a plan view of an additional embodiment of a disposable diaper of this invention with a portion broken away to show interior detail;

FIG. 9 is an enlarged cross-sectional view of the diaper of FIG. 8 taken along lines 9—9;

FIG. 10 is a plan view of another embodiment of the disposable diaper of the present invention;

FIG. 11 is an exploded perspective view of the elements of the diaper illustrated in FIG. 10;

FIG. 15 is a cross-sectional view taken along lines 15—15 of FIG. 14; and

FIG. 15A is an enlarged view of one end portion of FIG. 15.

DESCRIPTION OF THE PREFERRED EMBODIMENTS

For a disposable diaper of the present invention the gathering means is a plurality of readily stretchable, elastic, preferably thermoplastic members each of which possesses a certain minimum elastic recovery, and which co-operate to produce the same effect as a single width elastic member.

The term "elastic", as used herein, refers to sheets, films, ribbons and the like which have a recovery of at least 90 percent, when elongated at least 10 percent of their yield point and measured in accordance with the following formula:

$$\text{Percent retraction} = \frac{L_e - L_t \times 100}{L_e - L_o}$$

where
$L_o$=original length of sample
$L_e$=fully extended length
$L_t$=length of sample measured three seconds after released from extended length.

The thickness of the elastic members is generally 10 mils or less, and preferably about 0.5 to about 5 mils. The elastic members have an extensibility to rupture of at least about 300 percent, preferably about 400 to about 1000 percent and a recovery at 50 percent elongation of at least about 75 percent, and preferably at least about 80 percent. For ease of stretchability, the modulus of elasticity of the elastic member at 50 percent elongation should not exceed about 2000 pounds per square inch, and preferably is about 100 to about 200 pounds per square inch.

Figure 1:
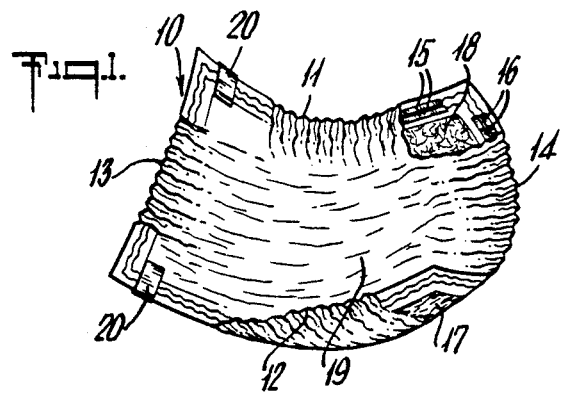
FIG. 1 is a perspective view illustrating one embodiment of a disposable diaper of the present invention with a portion broken away to show interior detail.

Referring to FIG. 1, disposable diaper 10 illustrating one embodiment of the present invention is provided with marginal longitudinal gathering means in opposite side margins 11 and 12 adapted to provide enhanced fit and gasketing about the baby's thighs. Additionally, optional transverse gathering means are provided in end margins 13 and 14 for enhanced fit about the baby's waist. The gathering means in each side margin include at least two separate and distinct longitudinally extending, effectively elastic elements such as elastic elements 15 in side margin 11. The optional transverse gathering means in the end margins of diaper 10 can be similar elastic elements such as elements 16 in end margin 14. Diaper 10 additionally includes first outer layer or backing 17 made of a moisture-impervious web, a generally rectangular absorbent panel 18 positioned in superposed relationship with respect to the backing, and second outer layer or facing 19 made of a moisture-pervious or permeable web and positioned in superposed relationship with respect to absorbent panel 18. For securement about a baby, diaper 10 is provided with pressure-sensitive adhesive tape tabs 20 and 21. The gathering means are generally parallel to the longitudinal side margins of panel 18, and when the gathering means are in a relaxed state, diaper 10 assumes a boat-like configuration as shown in FIG. 1, with side margins 11 and 12 having a reduced length.

Figure 2:
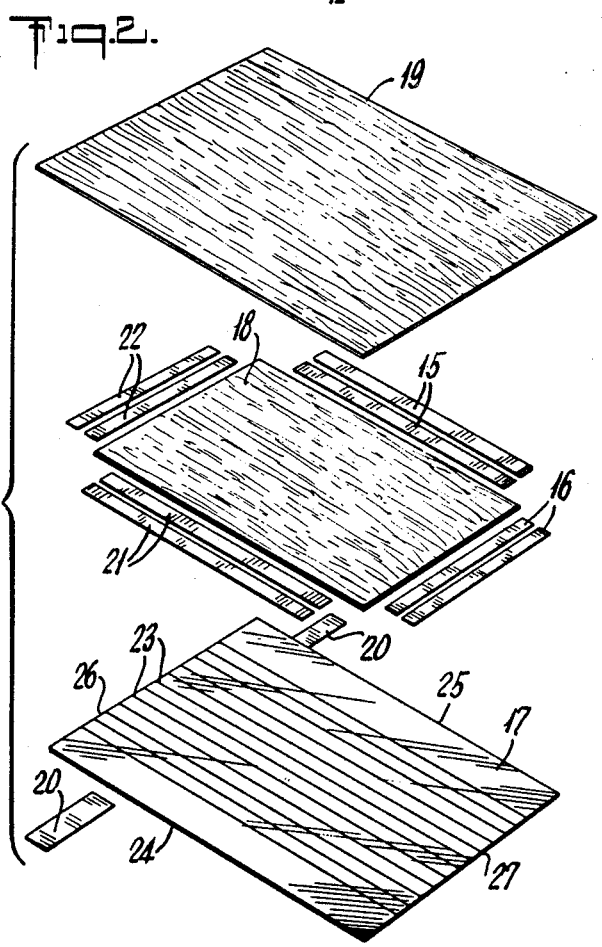
FIG. 2 is an exploded perspective view showing relative positioning of diaper elements during manufacture of the diaper depicted in FIG. 1.

The individual components of disposable diaper 10 are illustrated in FIG. 2. Absorbent panel 18 is superposed over backing 17 and is secured thereto by a series of glue lines 23 deposited on backing 17. Absorbent panel 18 is of smaller area than backing 17, and, when substantially centered on backing 17, is spaced from longitudinal sides 24 and 25 as well as transverse sides or ends 26 and 27 and thereby defines the side and end marginal portions of diaper 10.

Absorbent panel 18 is flanked on all four sides thereof by elastic elements 15, 16, 21 and 22 which, in an extended state, are secured to backing 17 by means of an elastic or inelastic adhesive, heat sealing, sonic sealing described below, or in any other convenient manner. Moisture-pervious facing 19 is superposed over absorbent panel 18, is larger in area than panel 18, and is secured to backing 17, usually by means of the exposed end portions of glue lines 23. However, other securement means can be utilized, if desired. Facing 19 may also be secured to elastic elements 15, 16, 21 and 22 in a manner similar to the securement thereof to backing 17.

As stated above, the elastic elements may be conveniently secured in place ultrasonically, such as by the use of apparatus of the type that is commercially available from Branson Instruments, Inc. of Stanford, Ct. Such apparatus conventionally includes an anvil and a horn that are positioned in juxtaposed relationship to one another, and the parts to be joined are inserted therebetween. The horn is energized to transmit vibrations in the ultrasonic frequency range into the parts to be joined. In the present instance, the elastic elements are elongated between backing layer 17 and facing layer 19, and the layers placed between a horn which coacts with an anvil which moves in registration with the product to provide spaced rows of simulated stitching. In this regard, the anvil of the ultrasonic sealing apparatus preferably is provided with a plurality of spaced land areas so that the stretched elastic elements are secured in place by a plurality of spaced securement zones. Spaced securement zones are also provided when the method of securement is heat sealing or inelastic adhesive. When elastic adhesive is used, lines of attachment may be continuous.

The configuration that disposable diaper 10 assumes when applied to a baby is illustrated in FIG. 3. Partially-extended diaper side margins 11 and 12 provide a comfortable yet positive seal about the baby's thighs that readily accommodates leg movements of the baby, while optional elastic elements in diaper end margins 13 and 14 assure good fit about the baby's waist.

FIG. 4 shows disposable diaper 30 that is similar to disposable diaper 10 but lacks the optional gathering means in diaper end margin 33. In the embodiment exemplified by FIG. 4, the gathering means in diaper end margin 34 is similar to gathering means 16 in FIG. 1 and performs in the same manner. The construction of diaper side margins 31 and 32 is substantially the same as in diaper side margins 11 and 12.

In the embodiment illustrated by FIG. 5 disposable diaper 60 is provided with absorbent panel 68 having curvilinear side cut-outs 71 and 72 and sandwiched between facing 69 and backing 67. Glue lines 65 serve to secure panel 68 and facing 69 to backing 67. Elastic elements 63 and 64 are situated in generally rectilinear diaper side margins 62 and 61. Elastic elements 63 and 64 extend substantially the entire length of diaper side margins 62 and 61, respectively, and are secured to backing 67 by spaced outer glue lines 77 and 78. Glue lines 77 are illustrated in cross-section in FIG. 6. The separate and distinct elastic elements of the gathering means provide separate lines of gathering or simulated gathered stitching which in turn create separate lines of gasketing of the puckered facing against the leg of the wearer. Protruding ears 73, 74, 75 and 76 of absorbent panel 68 overlap elastic elements 63 and 64 and provide additional absorbent capacity which can be readily utilized by building into absorbent panel 68 appropriate capillary transport means. Adhesive tape tab means 66 and 70 provide means for securing diaper 60 about a baby.

In the embodiment of FIG. 7, disposable diaper 80 is provided with substantially rectangular absorbent panel 88 having generally rectilinear sides, sandwiched between backing 87 and facing 89, and together with backing 87 and facing 89 defining diaper side margins 81 and 82. Curvilinear cut-outs 97 and 98 are provided in the respective central portions of margins 81 and 82 for further fit enhancement. Prestretched elastic elements 83a & 83b and 84a & 84b are positioned in respective margins 82 and 81 and are secured to backing 87 and facing 89 along the longitudinal sides of absorbent panel 88. In this particular embodiment, the inner elastic elements 83b and 84a are prestretched to a greater or larger degree of elongation than the outer elastic elements 83a and 84b; thus, though the inner and outer elastic elements may be of the same material and of the same width, the inner elastic elements will exhibit a different and greater degree of elasticity. Though in other instances it may be desirable to subject the outer elastic elements to a greater degree of elongation to achieve a greater degree of elasticity, in this embodiment, wherein the inner elastic elements lie close to or even underly the edge of the absorbent panel, a better fit is achieved when the inner elastic elements have a greater degree of elasticity so as to be able to contract the side edges of the absorbent panel. In this particular embodiment, the elastic elements have been prestretched to 80 percent elongation while the outer elastic elements have been prestretched to only 70 percent elongation, however the degree of elongation and the difference in degree of elongation between the inner and outer elastic elements will vary with the specification of the materials used in their configuration within the final diaper product. Glue lines 85 secure facing 89 and absorbent panel 88 to backing 87, and adhesive tape tabs 86 and 90 provide diaper securement means.

Yet another embodiment of a disposable diaper according to the present invention is shown in FIGS. 8 and 9 where disposable diaper 100 is provided with shaped absorbent panel 108 having curvilinear cut-outs 111 and 112 and centrally juxtaposed between backing 107 and facing 109. Both panel 108 and facing 109 are secured to backing 107 by a plurality of longitudinally extending glue lines 105. Curvilinear cut-outs 117 ane 118, similar in configuration but of smaller size than cut-outs 111 and 112, are provided in the side portions of facing 109 and backing 107 that form diaper side marginal portions 101 and 102, respectively, so that margin cut-out 117 subtends panel cut-out 111 and margin cut-out 118 subtends panel cut-out 112. Elastic elements 103 are positioned in diaper side marginal portions 102 between protruding ears 113 and 114 of absorbent panel 108 and are secured to facing 109 and backing 107 by spaced lines of attachment 119. In a similar manner, elastic elements 104 are positioned in diaper side marginal portion 101 between protruding ears 115 and 116 of absorbent panel 10S and are secured to facing 109 and backing 107. Facing 109 and backing 107 are not secured to each other in the side marginal portion between the gathering means and the longitudinal side edge of the diaper, creating a soft, ruffly side edge of the diaper. Diaper securement means are provided by adhesive tape tabs 106 and 110.

The separate and distinct multiple elastic elements create plural lines of sealing or gasketing about the leg of the wearer, aided by the puckering or gathering of the facing layer adjacent each elastic element, thereby providing improved liquid containment at the leg opening.

Referring now to FIGS. 10 and 11, a still further embodiment of the invention is illustrated in its entirety at 120, and includes a first outer layer 121 in the form of a moisture-pervious facing, a second outer layer 122 in the form of a moisture-impervious backing, a third layer 123 in the form of an absorbent panel sandwiched therebetween, and adhesive tape tabs 140. Outer layers 121 and 122 have the same outer dimensions and are coterminous with one another. Panel 123 has an external configuration similar to layers 121 and 122, and is smaller than and centered relative to layers 121 and 122. Parallel glue lines 124 on backing 122 secure the panel to the backing, and the outermost glue lines (and the ends of the intermediate glue lines) secure the portions of layers 121 and 122 that extend beyond panel 123 to one another.

The end portions 125 and 126 of panel 123 are generally equal in width and are wider than the panel mid-portion 127. For improved fit, the narrowest part 128 of the panel mid-portion is offset toward panel end portion 126, the portion that is adapted to be placed in front of the infant. Panel portion 128 is of relatively short length and is formed between parallel side edges 128a and 128b. Panel side edges 129, 130, 131 and 132 flare outwardly from the ends of edges 128a and 128b and terminate in end portion 129a parallel with end portion 131a and end portion 130a parallel with end portion 132a. In a most preferred embodiment of the invention, edges 129 and 131 are disposed at an angle of 25° and edges 130 and 132 are disposed at an angle of 35°, so that the included angle between edges 129 and 130 and edges 131 and 132 is 120°.

As with the previously described embodiments, diaper 120 includes gathering means 134 and 135 at opposite sides of the diaper, and optional gathering means 136 and 137 at opposite ends of the diaper. The illustrated gathering means are in the form of elongated elastic elements that are secured in a stretched condition to layers 121 and/or 122.

Figure 12:
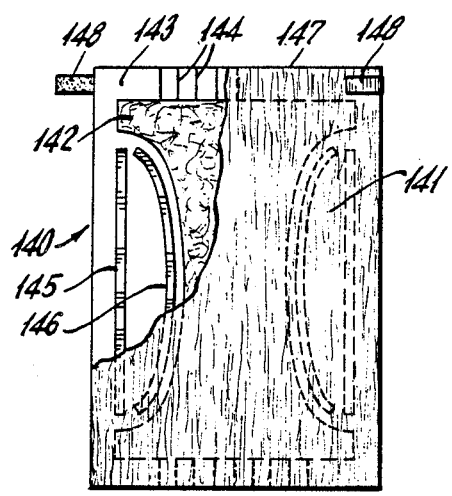
FIG. 12 is a plan view of yet another embodiment of the disposable diaper of the present invention.

Illustrated in FIG. 12 is a disposable diaper 140, with facing layer 141, and contoured absorbent panel 142 attached by glue lines 144 to backing layer 143. The gathering means in the side margin of the diaper includes two spaced elastic elements 145 and 146. The elastic elements are non-parallel. Elastic element 146 substantially parallels the contoured edge of the absorbent panel, while elastic elements 145 is substantially perpendicular to end edge 147 of the diaper. The diaper is provided with adhesive tape tab fasteners 148.

Figure 13:
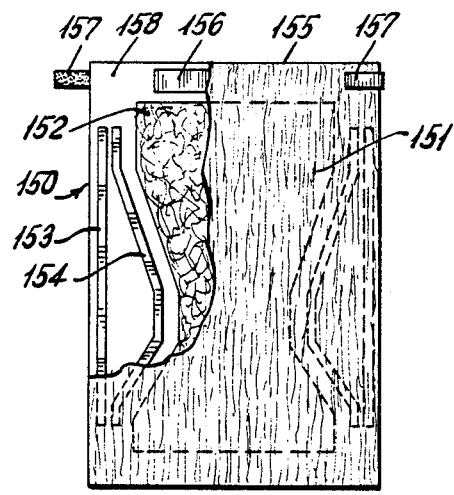
FIG. 13 is a plan view of still another embodiment of the disposable diaper of the present invention.

FIG. 13 illustrates a disposable diaper 150 wherein the elastic elements 153 and 154 of the gathering means in the side margin are parallel throughout only a portion of their length. Absorbent panel 152 is essentially hourglass in shape, and has a more sharply defined contour in the crotch portion as opposed to the gently curving contour of absorbent panel 142 of FIG. 12. The elastic elements 153 and 154 are substantially parallel at the end portions of the diaper. Through the crotch portion of the diaper, elastic element 154 parallels the edge of the hourglass shaped absorbent panel, continues in a substantially straight line, substantially perpendicular to the end edge 155 of the diaper. The diaper is also provided with facing layer 151, backing layer 158, adhesive tape tabs 158, and optionally, gathering means 156 in at least one end margin.

Figure 14:
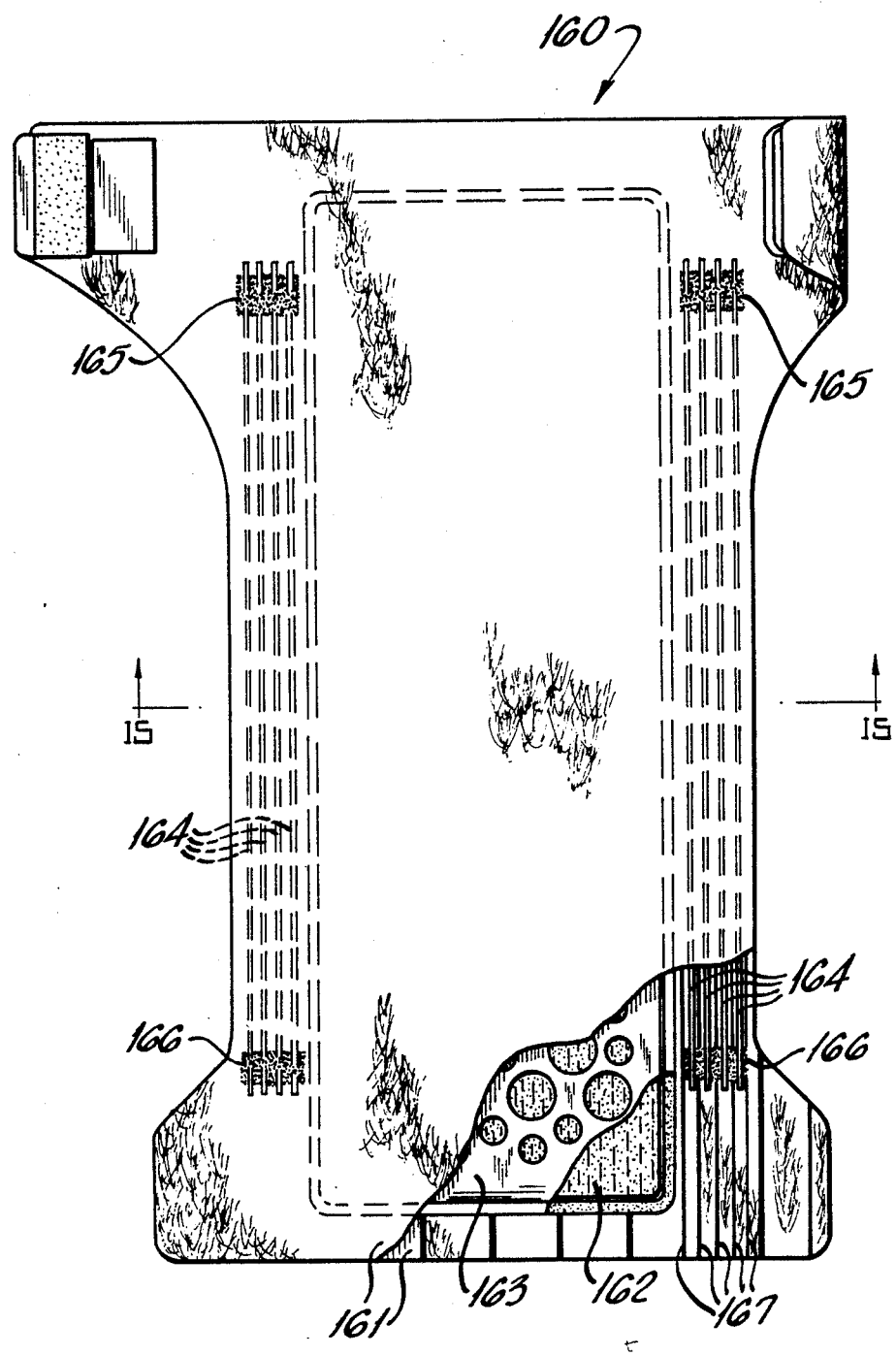
FIG. 14 is a plan view with a portion broken away for clarity of a further embodiment of the disposable diaper of the present invention.

FIG. 14 depicts a diaper 160 having two layers of liquid-permeable fabric 161 with an absorbent core disposed in between the layers of fabric. The layers of fabric extend beyond the absorbent core thus providing side and end margins. The absorbent core contains an absorbent batt 162 enveloped in a liquid-impermeable film or fabric 163. The envelope 163 contains holes for ingress of liquid. Four elastic elements 164 are stretched and placed in each side margin. These elements are secured at each end in regions 165 and 166. These securement regions are provided by adhesive or heat application (if the elastic elements are thermoplastic) or a suitable means for adhering the end portion of the elastic elements 164 to the liquid-permeable fabric 161. Glue lines 167 are registered on the liquid-permeable fabric 161 so as to pass between the elastic elements 164 when adhering the two layers of liquid-permeable fabric 161 to each other in the margins. As a result channels are created for the unsecured portion of the elastic elements 164.

FIG. 15, which is a cross-sectional view along line 155—15 of FIG. 14, shows the elastic elements 164, designated 174 in FIG. 15, 174 lying in the channels created by the glue lines 167, designated 177 in FIG. 15, which adhere the two layers of liquid-permeable fabric 161 to one another in the margins. The absorbent batt 162, designated 172 in FIG. 15, is enveloped by a liquid-impermeable film 163, designated 173 in FIG. 15, or the like.

In FIG. 15A, reference numerals correspond to those in FIG. 15 followed by the designation "A".

FIG. 15A provides an enlarged view of the elastic elements 174A in channels provided by glue lines 177A to adhere the liquid-permeable layers 171A to one another.

The envelope of liquid-impermeable film 173A encompasses the absorbent batt 172A and is provided with slits or holes for ingress of liquid.

The means of securing the elastic elements only at their end portions may be extended to any diaper configuration wherein marginal lamination takes place. For instance, a polyethylene backing laminated to a polyester facing provides a proper environment for adhering the elastic elements only at their end portions.

Elastic film elements suitable as gathering means for the diapers contemplated herein can be extruded to the desired thickness utilizing unvulcanized, thermoplastic compositions which are made up of an elastomeric component and an optional compatible modifier which is a thermoplastic polymer of a relatively low molecular weight but solid at ambient temperature.

Illustrative of the elastomeric components suitable for present purposes are block copolymers which comprise terminal thermoplastic polymer blocks and at least one non-terminal or intermediate elastomeric polymer block. Block copolymers of this general type may be prepared using a step-wise polymerization initiator, e.g., an organolithium compound. Such block polymerization techniques are well known in the art.

The elastomeric component can be linear or radial $A^1$-B-$A^2$ block copolymers or mixtures thereof with simple $A^1$-B block copolymers where $A^1$ and $A^2$ can be alike or different and represent a thermoplastic polymer block, such as poly(vinylarene) block, and B represents an elastomeric polymer block such as a conjugated diene or a lower (i.e., $C_1$–$C_4$) alkene. The modifier component is a low molecular weight thermoplastic polymer having an average molecular weight of about 500 to about 7500 and is present in the composition in an amount of about 0 to about 200 parts by weight per 100 parts by weight of the elastomeric component.

A preferred thermoplastic film composition for the elastic film elements comprises an elastomeric component which contains, as a major constituent thereof, an unvulcanized linear block copolymer of the general configuration $A^1$-B-$A^2$ wherein $A^1$, $A^2$ and B have the same meaning as hereinabove. In these block copolymers the A-blocks are derived from styrene or styrene homologues, and the B-blocks are derived from conjugated dienes or lower alkenes. The thermoplastic polymer modifier is compatible with the elastomeric component and associates principally with the thermoplastic terminal blocks of the aforesaid unvulcanized block copolymer. The thermoplastic polymer modifier preferably has an average molecular weight of about 1000 to 3000, and is present in the film composition in an amount of about 80 to about 200 parts by weight per 100 parts by weight of the elastomeric component.

The preferred $A^1$-B-$A^2$ block copolymers have A-blocks derived, i.e., polymerized or copolymerized, from styrene or styrene homologues; and B-blocks derived from conjugated dienes, such as isoprene or butadiene, or from lower alkenes, such as ethylene and butylene. Small proportions of other monomers also may enter into the block copolymers themselves. The individual A-blocks can have an average molecular weight of at least about 6000, preferably in the range of about 8000–30,000, and the A-blocks constitute about 51 ∝ 50 percent, preferably about 10–30 percent, by weight of the block copolymer. The average molecular weight of the B-blocks for linear $A^1$-B-$A^2$ copolymers preferably is in the range of about 45,000–180,000 and that of the linear copolymer itself, preferably is in the range of about 75,000–200,000. The average molecular weight of the radial $A^1$-B-$A^2$ block copolymers preferably is in the range of about 125,000–400,000. The term "linear block copolymer" (or copolymers) includes branched $A^1$-B-$A^2$ copolymers as well as unbranched $A^1$-B-$A^2$ copolymers.

The radial $A^1$-B-$A^2$ copolymers useful for manufacture of elastic elements for diapers of this invention are of the type described in United States Letters Pat. No. 3,281,383 to Zelinski el al and conform to the following general formula: $(A-B-)_n X$, wherein A is a thermoplastic block polymerized from styrene or styrene homologues, B is an elastomeric block derived from conjugated dienes or lower alkenes, as indicated above, X is an organic or inorganic connecting molecule, with a functionality of about 2 to 4 as described in U.S. Pat. No. 3,281,383, or possibly with a higher functionality as described in the article entitled "New Rubber is Backed by Stars" appearing on Page 35 of the June 11, 1975 issue of Chemical Week. As used hereinabove, "n" has a value corresponding to the functionality of X.

The preferred elastic film elements are highly thermoplastic and, though elastomeric, are unlike rubber in that the film exhibits a relatively sharp melting point and is capable of being heat shaped. Also, the elastic elements can form permanent heat seals to substrates such as nonwoven fabrics, or the like, at relatively low heat sealing peak temperatures, generally not above about 350° F. The elements are highly elastic and have a relatively low rubber modulus, i.e., they exhibit in at least one direction an elastic recovery from 50 percent stretch to at least 75 percent, preferably at least about 80 percent, and a 50 percent rubber modulus of not above about 2000 pounds per square inch, preferably not above 1000 pounds per square inch at 50 percent elongation. The film elements also are very flexible, extensible and soft and normally exhibits a Gurley stiffness of about one or less at a film thickness of one mil, and an elongation to break of at least about 300 percent, preferably at least about 400 percent, in at least one direction at ambient temperatures.

Several different types of facing materials may be used for diaper facing. For example, the facing may be a nonwoven web made up of a mixture of fibers consisting predominantly of inexpensive short cellulosic fibers such as wood pulp fibers or cotton linters, in amounts of about 75 percent to about 98 percent, the balance being textile length fibers such as rayon as described in U.S. Pat. No. 3,633,348 to Liloia et al.

Non-woven facing materials suitable for use in disposable diapers of this invention can have fabric weights in the range of about, 0.5 to 5 oz./yd.$^2$ and densities of less than 0.15 g./cc., generally in the range of about 0.05 to about 0.1 g./cc. The dry strength of the facing sheet for a fabric having a weight of about 1.5 oz./yd.$^2$ is at least 0.15 lbs./in. of width in the machine direction and at least 0.1 lbs./in. of width in the cross direction. Such fabrics have unusually good elongation, loft, softness, and drape characteristics.

Facings may also be made of an apertured non-woven fabric which is formed, for example, in accordance with the teachings of commonly assigned U.S. Pat. Nos. 2,862,251; 3,081,514 and 3,081,515. Briefly, such fabrics are foraminous structures wherein groups or groupings of fibers have been rearranged from a fibrous non-woven starting web into positions surrounding less dense fabric portions by passage of a fluid through the starting material. The fibers within the groupings are mechanically interlocked, and may be arranged into various patterns, as is well known by those skilled in the art. A suitable binder may be utilized to help retain the fibers in their rearranged locations, as is also well known by those skilled in the art. The fabric can be made of naturally occurring fibers, synthethic fibers, or blends thereof. Typical facing sheets made of a fibrous polyester type material can have a weight of about 0.75 oz./yd.$^2$.

In addition, facings can be formed of a non-aperatured material, such as a non-woven isotropic web, or of an apertured polyolefin or polyester film having the desired moisture permeability. In all of the aforementioned facings the material should be relatively hydrophobic so as to retard wicking within the facing.

The moisture-absorbent batt or panel of a desired shape but smaller than the facing and the backing, can be formed in accordance with the teachings of U.S. Pat. No. 3,612,055 to Mesek et al.

A suitable backing material for the diapers embodying the present invention can be an opaque polyolefin, e.g., polyethylene, web about 0.001 inch thick. Another suitable material for this purpose is a polyethylene terephthalate web having a thickness of about 0.0005 inch.

In use, the disposable diaper is applied to the baby by laying out the diaper on a suitable flat surface and placing the baby thereon so that the waist-underlying end of the diaper is that having the fastener means. The other end of the diaper then extends downwardly between the infant's legs. Next, the downwardly extending end of the diaper is brought up between the baby's legs to a position covering the perineum and contiguous with the front portion of the baby's waist. The diaper is thereafter secured to the baby by placing the corners of the waist portion of the abdomen-covering end as far around the baby's waist as they will go and by bringing the corners of the underlying end of the diaper into an overlapping relationship with the aforementioned corners so that the diaper snugly encircles the baby's waist and provides a custom fit. The adhesive tab fasteners are then prepared for use and the diaper is secured in the desired position by simply urging the pressure-sensitive adhesive surface of the tape tab in contact with the adjacent outer surface of the opposite corner of the diaper. The applied diaper assumes a configuration such as shown in FIG. 3.

The foregoing description and the drawings are illustrative and are not to be taken as limiting. Still other variations and modifications are possible without departing from the spirit and scope of the present invention.

What is claimed is:

1. A disposable diaper comprising:
a moisture-permeable facing layer; an absorbent panel at one side of said facing layer, said absorbent panel being smaller than said facing layer so that side marginal portions of the facing layer extend outwardly beyond the side edges of said absorbent panel; a backing layer at the side of said absorbent panel opposite said facing layer, said backing layer being larger than said absorbent panel so that side marginal portions of the backing layer extend outwardly beyond the side edges of said absorbent panel and into juxtaposed relationship with respect to the side marginal portions of said facing layer; means bonding said facing and backing layers to one another; and gathering means disposed between the juxtaposed side marginal portions of said backing and facing layers at each side edge of said absorbent panel, each of said gathering means including at least two spaced separate and distinct longitudinally extending, effectively elastic elements secured in between said juxtaposed side marginal portions by means securing said separate elastic elements in spaced relation to each other to at least one of said facing layer and said backing layer to thereby define a region of said one layer between adjacent ones of said elastic elements which said region is unsecured to any of said elastic elements, whereby said gathering means provide improved conformity about the legs of the wearer without undue application of pressure upon the skin of the wearer and each of said elastic elements applies a gathering forces to a zone of at least one of said juxtaposed side marginal portions thereby defining a plurality of gasketing lines at the leg of the wearer for improved liquid containment, said plurality of gasketing lines corresponding in number and spacing to said elastic elements, said region of said one layer being disposed between adjacent ones of said gasketing lines, each elastic element having a recovery of at least 90 percent when elongated at least 10 percent of its yield point and measured in accordance with:

$$\text{Recovery (percent retraction)} = \frac{(L_e - L_t) \times 100}{L_e - L_o}$$

where $L_o$ equals the original length of the sample, $L_e$ equals the fully extended length, and $L_t$ 1 equals the length of the sample measured three seconds after released from extended length.

2. A disposable diaper as in claim 1 wherein the elastic elements are secured to both the facing layer and backing layer.

3. A disposable diaper as in claim 1 wherein the elastic elements are secured by said securing means in spaced relation to each other only at their end regions.

4. A disposable diaper as in claim 1 wherein the elastic elements in between said respective side marginal portions are disposed in parallel relationship one to the other along their entire length.

5. A disposable diaper as in claim 1 wherein at least one of the elastic elements in between said respective side marginal portions is disposed parallel to a side edge of the diaper.

6. A disposable diaper comprising: a moisture-permeable facing layer; an absorbent panel at one side of said facing layer, said absorbent panel being smaller than said facing layer so that marginal portions of the facing layer extend outwardly beyond the edges of said absorbent panel; a moisture-impermeable backing layer at the side of said absorbent panel opposite said facing layer, said backing layer being larger than said absorbent panel so that marginal portions of the backing layer extend outwardly beyond the edges of said absorbent panel; means bonding said facing and backing layers to one another; and gathering means disposed juxtaposed to at least one said marginal portion, said gathering means including at least two spaced longitudinally extending effectively elastic elements secured in juxtaposed to said one marginal portion by means securing said separate elastic elements in spaced relation to each other to at least one of said facing layer and said backing layer to thereby define a region of said one layer between adjacent ones of said elastic elements which said region is unsecured to any of said elastic elements, whereby said gathering means provides improved body conformity without undue application of pressure upon the skin of the wearer by providing a plurality of gasketing lines corresponding in number and spacing to said elastic elements, each elastic element having a recovery of at least 90 percent when elongated at least 10 percent of its yield point and measured in accordance with:

$$\text{Recovery (percent retraction)} = \frac{(L_e - L_t) \times 100}{L_e - L_o}$$

where $L_o$ equals the original length of the sample, $L_e$ equals the fully extended length, and $L_t$ equals the length of the sample measured three seconds after released from extended length.

7. A disposable diaper as in claim 6 wherein the elastic elements are disposed between the facing layer and for backing layer.

8. A disposable diaper as in claim 7 wherein the elastic elements are secured to both the facing layer and the backing layer.

9. A disposable diaper as in claim 6 wherein the elastic elements juxtaposed to said one marginal portion are disposed in parallel relationship one to the other.

10. A disposable diaper comprising two liquid-permeable layers of fabric containing therebetween an absorbent core of lesser size than said fabric layers resulting in at least one marginal portion of said diaper wherein said fabric layers are superposed, said absorbent core having a liquid-impermeable envelope, with slits or openings, enveloping an absorbent batt; and gathering means disposed in said marginal portion, said gathering means including at least two spaced, separate, and distinct effectively elastic elements disposed in said marginal portion, said elastic elements being secured only at their end portions by means securing said elastic elements in spaced relation to each other to at least one of said fabric layers to thereby define a region of said one layer which said region is unsecured to any of said elastic elements, whereby each elastic element of said gathering means applies a gathering force to a zone of said marginal portion thereby defining a plurality of gasketing lines within said marginal portion corresponding in number and spacing to said elastic elements, said region of said one fabric layer being disposed between adjacent ones of said gasketing lines, each elastic element having a recovery of at least 90 percent when elongated at least 10 percent of its yield point and measured in accordance with:

$$\text{Recovery (percent retraction)} = \frac{(L_e - L_t) \times 100}{L_e - L_o}$$

where $L_o$ equals the original length of the same, $L_e$ equals the fully extended length, and $L_t$ equals the length of the sample measured three seconds after released from extended length.

11. A disposable diaper as in claim 1, wherein said securing means comprises means individually securing each said elastic element along at least a central portion of its length.

12. A disposable diaper as in claim 11, wherein said means individually securing each said elastic element comprises a plurality of spaced securement zones securing each said elastic element along at least the central portion of its length.

13. A disposable diaper as in claim 3, wherein said elastic elements are respectively disposed in channels defined by a plurality of spaced glue lines adhering said backing layer to said facing layer.

14. A disposable diaper as in claim 10, wherein said elastic elements are respectively disposed in channels defined by a plurality of spaced glue lines adhering said fabric layers to each other.

15. A disposable diaper comprising: a backing layer; an absorbent panel at one side of said backing layer; a moisture-permeable facing layer at the side of said absorbent panel opposite said backing layer; means bonding said facing and backing layers to one another; and gathering means juxtaposed to a portion of at least one of said backing and facing layers, said gathering means including a plurality of spaced separate and distinct longitudinally extending, effectively elastic elements juxtaposed to said portion of said one of said backing and facing layers; means securing said plurality of separate elastic elements in spaced relation to each other to said one of said backing and facing layers to thereby define a region of said one layer between adjacent ones of said elastic elements which said region is unsecured to any of said elastic elements, whereby said gathering means provides improved conformity to the wearer without undue application of pressure upon the skin of the wearer, and each of said elastic elements applies a gathering force to a zone of said portion of said one layer to thereby define a plurality of gasketing lines at the skin of the wearer for improved liquid containment, said plurality of gasketing lines corresponding in number and spacing to said plurality of elastic elements, said region of said one layer being disposed between adjacent ones of said gasketing lines, each elastic element having a recovery of at least 90 percent when elongated at least 10 percent of its yield point and measured in accordance with:

$$\text{Recovery (percent retraction)} = \frac{(L_e - L_t) \times 100}{L_e - L_o}$$

where $L_o$ equals the original length of the sample, $L_e$ equals the fully extended length, and $L_t$ equals the length of the sample measured three seconds after released from extended length.

16. A disposable diaper as in claim 15, wherein said plurality of elastic elements juxtaposed to said portion of said one layer are positioned between said one layer and a portion of the other one of said layers juxtaposed to said elastic elements and to said portion of said one layer.

17. A disposable diaper as in claim 15, wherein said means securing said elastic elements comprises means individually securing each said element along at least a central portion of its length.

18. A disposable diaper as in claim 17, wherein said means individually securing each said elastic element comprises a plurality of spaced securement zones securing each said elastic element along at least the central portion of tis length.

19. A disposable diaper as in claim 15, wherein said means securing said elastic element comprises means securing said elastic elements only at their end regions.

20. A disposable diaper as in claim 19, wherein said elastic elements are positioned between said one layer and a portion of the other one of said other layers juxtaposed to said elastic elements and to said portion of said one layer, said elastic elements being respectively disposed in channels defined by a plurality of spaced glue lines adhering said portion of said other layer to said one layer.

21. A disposable diaper as in claim 16, wherein said plurality of elastic elements of said gathering means are secured by said securing means to each of said facing layer and said backing layer.

22. A disposable diaper as in claim 15, wherein the elastic elements to said gathering means are disposed in parallel relationship to one another along at least a portion of their length.

23. A disposable diaper comprising: a backing layer; an absorbent panel at one side of said backing layer; a moisture-permeable facing layer at the side of said absorbent panel opposite said backing layer, at least one of said facing layer and said backing layers being larger than said absorbent panel so that side marginal portions of said one layer extend outwardly beyond the side edges of said absorbent panel; means bonding said facing and backing layers to one another; and gathering means disposed at each said side marginal portion, each said gathering means including a plurality of spaced separate and distinct longitudinally extending, effectively elastic elements disposed at the respective side marginal portion; means securing said plurality of separate elastic elements in spaced relation to each other to said one of said backing and facing layers to thereby define a region of said one layer between adjacent ones of said elastic elements which said region is unsecured to any of said elastic elements, whereby said gathering means provides improved conformity about the legs of the wearer without undue application of pressure upon the skin of the wearer and each of said elastic elements applies a gathering force to a zone of the respective side marginal portion of said one layer to thereby define a plurality of gasketing lines at the leg of the wearer for improved liquid containment, said plurality of gasketing lines corresponding in number and spacing to said plurality of elastic elements, said region of said one layer being disposed between adjacent ones of said gasketing lines, each elastic element having a recovery of at least 90 percent when elongated at least 10 percent of its yield point and measured in accordance with:

$$\text{Recovery (percent retraction)} = \frac{(L_e - L_t) \times 100}{L_e - L_o}$$

where $L_o$ equals the original length of the sample, $L_e$ equals the fully extended length, and $L_t$ equals the length of the sample measured three seconds after released from extended length.

24. A disposable diaper comprising: a moisture impermeable backing layer; an absorbent panel at one side of said backing layer, said absorbent panel being smaller than said backing layer so that opposite side marginal portions of the backing layer extend outwardly beyond respective side edges of said absorbent panel; a moisture-permeable facing layer at the side of said absorbent panel opposite said backing layer; means bonding said facing and backing layers to one another; and a pair of gathering means respectively juxtaposed to said side marginal portions of said backing layer, said gathering means each including a plurality of spaced separate and distinct longitudinally extending, effectively elastic elements arranged in parallel relation to each other; means securing said plurality of separate elastic elements in spaced relation to each other to at least said backing layer to thereby define a region of said backing layer between adjacent ones of said elastic elements which said region is unsecured to any of said elastic elements, whereby each said gathering means provides improved conformity about the leg of the wearer without undue application of pressure upon the skin of the wearer, and each of said elastic elements applies a gathering force to a zone of the respective marginal portion to there by define a plurality of gasketing lines at the leg of the wearer for improved liquid containment, said plurality of gasketing lines corresponding in number and spacing to said plurality of elastic elements, said region of said backing layer being disposed between adjacent ones of said gasketing lines, each elastic element having a recovery of at least 90 percent when elongated at least 10 percent of its yield point and measured in accordance with:

$$\text{Recovery (percent retraction)} = \frac{(Le - Lt) \times 100}{Le - Lo}$$

where $L_o$ equals the original length of the sample, $L_e$ equals the fully extended length, and $L_t$ equals the length of the sample measured three seconds after released from extended length.

25. A disposable diaper as in claim 24, wherein said elastic elements of each gathering means are positioned between the respective one of said marginal portions and a portion of said facing layer.

26. A disposable diaper as in claim 24, wherein said means securing said elastic elements comprises means individually securing each said elastic element along at least a central portion of its length.

27. A disposable diaper as in claim 26, wherein said means individually securing each said elastic element comprises a plurality of spaced securement zones securing each said elastic element along at least the central portion of its length.

28. A disposable diaper comprising: a backing layer; an absorbent panel at one side of said backing layer; a moisture-permeable facing layer at the side of said absorbent panel opposite said backing layer; means bonding said facing and backing layers to one another; and gathering means operatively connected to at least said facing layer, said gathering means including a plurality of spaced separate and distinct longitudinally extending, effectively elastic elements operatively connected to said facing layer; means securing said plurality of separate elastic elements in spaced relation to each other to said facing layer, at least one of said elastic elements connected to said facing layer being positioned between said facing layer and said backing layer, whereby said gathering means provides improved conformity to the wearer without undue application of pressure upon the skin of the wearer, and each of said elastic elements applies a gathering force to thereby define a plurality of gasketing lines at the skin of the wearer for improved liquid containment, said plurality of gasketing lines corresponding in number and spacing to said plurality of elastic elements, each elastic element having a recovery of at least 90 percent when elongated at least 10 percent of its yield point and measured in accordance with:

$$\text{Recovery (percent retraction)} = \frac{(Le - Lt) \times 100}{Le - Lo}$$

where $L_o$ equals the original length of the sample, $L_e$ equals the fully extended length, and $L_t$ equals the length of the sample measured three seconds after released from extended length.

29. A disposable diaper as in claim 28, wherein at least one of said elastic elements is positioned laterally outwardly of said absorbent panel of said disposable diaper.

30. A disposable diaper as in claim 28, wherein at least one of said elastic elements is secured directly to said facing layer.

31. The disposable diaper in accordance with claim 28, wherein
one of said elastic elements of said gathering means has a different degree of elastically than another one of the elastic elements of said gathering means.

32. The disposable in accordance with claim 28, wherein
one of said elastic elements of said gathering means is disposed outwardly of another elastic element to said gathering means, and has a greater degree of elasticity.

33. The disposable diaper as in claim 1, 6, 10, 15, 23, 24 or 28, wherein
each elastic element is formed of a thermoplastic material.

34. The disposable diaper in accordance with claim 28, wherein
each elastic element is formed of a thermoplastic material, and at least one of said elastic elements comprises elastic material in the form of an A-B-A block copolymer.

* * * * *